(12) United States Patent
Jaynes et al.

(10) Patent No.: US 11,591,161 B2
(45) Date of Patent: Feb. 28, 2023

(54) APPARATUSES, SYSTEMS, AND METHODS FOR STORAGE AND DISPENSING OF ARTICLES

(71) Applicant: OMNICELL, INC., Mountain View, CA (US)

(72) Inventors: Robert Warren Jaynes, Mars, PA (US); Michael Edward McGregor, Baden, PA (US)

(73) Assignee: OMNICELL, INC., Mountain View, CA (US)

( * ) Notice: Subject to any disclaimer, the term of this patent is extended or adjusted under 35 U.S.C. 154(b) by 0 days.

(21) Appl. No.: 16/826,937

(22) Filed: Mar. 23, 2020

(65) Prior Publication Data

US 2021/0292091 A1    Sep. 23, 2021

(51) Int. Cl.
*B65G 1/137* (2006.01)
*B65G 1/06* (2006.01)
*B65G 1/12* (2006.01)
*B65G 1/04* (2006.01)

(52) U.S. Cl.
CPC ............. *B65G 1/1375* (2013.01); *B65G 1/06* (2013.01); *B65G 1/12* (2013.01); *B65G 1/1371* (2013.01); *B65G 1/0492* (2013.01)

(58) Field of Classification Search
CPC combination set(s) only.
See application file for complete search history.

(56) References Cited

U.S. PATENT DOCUMENTS

| | | | |
|---|---|---|---|
| 5,468,110 A | 11/1995 | McDonald et al. | |
| 8,252,232 B2 | 8/2012 | Neeper et al. | |
| 8,483,867 B2 | 7/2013 | Braun et al. | |
| 10,586,418 B2 | 3/2020 | Greyshock et al. | |
| 2001/0032035 A1* | 10/2001 | Holmes | A47B 88/994 700/231 |
| 2007/0135965 A1* | 6/2007 | Nguyen | G16H 20/13 700/231 |

(Continued)

FOREIGN PATENT DOCUMENTS

| CN | 206 358 922 U | 7/2017 |
|---|---|---|
| CN | 206 375 266 U | 8/2017 |

(Continued)

OTHER PUBLICATIONS

International Search Report and Written Opinion (ISA/EP) for PCT/US2021/016229 completed 19 Apr. 29, 2021 (12 pages).

*Primary Examiner* — Kyle O Logan
(74) *Attorney, Agent, or Firm* — Alston & Bird LLP

(57) ABSTRACT

Provided herein is a methods, apparatus, and system for the configuration of customizable trays for the storage and dispensing of articles. Methods may include: receiving an indication of a plurality of articles to be stored in a tray; determining a plurality of bins corresponding to the plurality of articles; generating a layout of the bins on the tray; identifying locations of the plurality of articles within the bins on the tray; and causing the tray to be configured according to the layout of the plurality of bins on the tray. Methods may include: receiving an indication of an article to be loaded into a bin of the plurality of bins; receiving a unique identifier of the bin of the plurality of bins into which the article is loaded; and storing, in a memory, a correlation between the unique identifier of the bin and the article loaded into the bin.

20 Claims, 11 Drawing Sheets

(56) References Cited

U.S. PATENT DOCUMENTS

| | | |
|---|---|---|
| 2010/0030667 A1 | 2/2010 | Chudy et al. |
| 2010/0042255 A1 | 2/2010 | Boutin et al. |
| 2012/0029687 A1* | 2/2012 | Hagen .................. G07F 11/165 |
| | | 700/218 |
| 2013/0126547 A1 | 5/2013 | Kim |
| 2013/0287537 A1 | 10/2013 | Hecht et al. |
| 2014/0262690 A1 | 9/2014 | Henderson |
| 2015/0308466 A1 | 10/2015 | Girtman |
| 2016/0327941 A1 | 11/2016 | Stiernagle et al. |
| 2017/0043953 A1* | 2/2017 | Battles .................... B65G 1/04 |
| 2017/0246083 A1 | 8/2017 | Amano et al. |
| 2018/0305125 A1 | 10/2018 | Guo et al. |

FOREIGN PATENT DOCUMENTS

| | | |
|---|---|---|
| WO | WO 2017/081281 A1 | 5/2017 |
| WO | WO-2019/093413 A1 | 5/2019 |

* cited by examiner

APPARATUSES, SYSTEMS, AND METHODS FOR STORAGE AND DISPENSING OF ARTICLES

TECHNOLOGICAL FIELD

Embodiments of the present invention relate generally to the storage and dispensing of articles, and in particular, to the storage and dispensing of articles from user-configurable and customizable trays, and the software to configure these trays.

BACKGROUND

The storage and dispensing of goods is a common practice that can often be time consuming and inefficient. Automated and semi-automated dispensing systems can improve the efficiency of dispensing and reduce potential errors leading to improved throughput. Systems configured to store and dispense articles of differing shapes and sizes often default to an organizational strategy of placing similarly sized articles together regardless of the most efficient and useful arrangement of articles.

While some articles that are stored and dispensed may be suitable for co-mingling in various sizes of containers, articles such as medications may require more care to ensure accurate tracking and dispensing of articles that may affect an individual's health. Storage of healthcare related articles may include storing similarly sized articles in trays for articles of that common size, while the efficiency of the arrangement of the stored articles is of a lower priority than the convenience of storing like-sized articles together. Such storage can reduce the efficiency of dispensing, and may impact the availability of storage space for specific types of articles.

SUMMARY

Embodiments of the present disclosure may provide an apparatus for the storage and dispensing of articles, and in particular, for the storage and dispensing of articles from user-configurable and customizable trays, and the software to configure these trays. Embodiments of the present disclosure may include a system for configuring trays for storage and dispensing of articles. The system may include: a configuration interface adapted to receive at least one input parameter to determine a storage configuration for one or more trays adapted to engage with a dispensing system, each of the one or more trays adapted to hold one or more articles; and a configurator module, further comprising processing circuitry, adapted to generate a recommended layout for the one or more trays for securely holding the one or more articles based on the one or more input parameters, where for each of the one or more articles, the one or more input parameters includes at least one of the following: type of the article, size of the article, capacity of the article, identification of the article, volume of contents held within the article, characteristics of the tray, and available space in the dispensing system.

According to an example embodiment, the recommended layout for the one or more trays specifies at least one of: number of separators; orientation of the separators; or location of placement of the separators. The recommended layout for each of the one or more trays includes a recommended layout of bins and specifies at least one of: a number of bins, a size for each of the bins, a quantity of the one or more articles that can be held within each of the bins, a number of trays needed to hold the one or more articles, and a relative positioning of the one or more bins within the recommended layout. The processing circuitry may further be configured to: receive an indication of an article to be loaded into a bin of the layout of bins; receive a unique identifier of the bin of the layout of bins into which the article is loaded; and store, in a memory, a correlation between the unique identifier of the bin and the article loaded into the bin.

The processing circuitry of some embodiments may be configured to: receive an indication of a unique identifier of a tray corresponding to the layout of bins; and correlate the unique identifier of the bin and the article loaded into the bin with the unique identifier of the tray. The processing circuitry configured to generate the recommended layout of bins for securely holding the one or more articles may include processing circuitry configured to: determine a size of each of the one or more articles; and identify, for each of the one or more articles, a bin size appropriate for the respective article. The processing circuitry configured to generate a recommended layout may include processing circuitry configured to: generate a recommended layout using one or more separators forming one or more bins on a tray, the layout further including a position and an orientation for each of the one or more bins on the tray.

The configuration interface to receive at least one input parameter to determine a storage configuration for the one or more trays may include: a user interface element to select a type of article; a user interface element to select a quantity of a type of article and a user interface element to add the quantity of the type of article to a list of the one or more articles to be stored in a tray. The processing circuitry may be configured to provide instruction for configuration of the recommended layout for the one or more trays; and cause the configuration of the recommended layout for the one or more trays to be assembled. The processing circuitry may be configured to cause the one or more articles to be dispensed and arranged according to the recommended layout.

Embodiments provided herein may include a method for configuring one or more trays, including: receiving information about one or more articles to be stored in the one or more trays; selecting one or more separators or bins to hold the one or more articles based on data representing characteristics of at least the one or more items and characteristics of the one or more trays; determining a layout map for the one or more trays using at least characteristics of the one or more articles; and generating a tray layout to hold the one or more articles. Methods may include: identifying locations for the one or more articles within the tray layout; and causing the one or more trays to be configured according to the tray layout.

Methods may include: receiving an indication of an article to be loaded into a location within the tray layout; receiving a unique identifier of the location into which the article is loaded; and storing, in a memory, a correlation between the unique identifier of the location and the article loaded into the location. Methods may include receiving an indication of a unique identifier of a tray corresponding to the location into which the article is loaded, and correlating the unique identifier of the location and the article loaded into the location with the unique identifier of the tray. Determining the layout map for the tray may include: determining a size of each of the one or more articles; and identifying, for each of the one or more articles, a bin size appropriate for the respective article. Generating the layout map for the one or more trays may include: generating a layout of the plurality of the one or more separators or bins on the tray including a position and an orientation of the one or more separators or bins on the tray.

According to an example embodiment, receiving information about one or more articles to be stored in the one or more trays may include: receiving selection of a type of article; receiving selection of a quantity of the type of article; and receiving an indication to add the quantity of the type of article to a list of the plurality of articles to be stored in the one or more trays. Methods may include: determining if a configured tray is configured according to the layout map; and providing an alert in response to the configured tray not being configured according to the layout. Methods may include: providing instruction for configuration of the layout map for the one or more trays; and causing the configuration of the layout map to be assembled.

Embodiments provided herein may include an apparatus having at least one processor and at least one non-transitory computer readable storage medium having computer program code instructions stored thereon, with the at least one processor configured to, upon execution of the program code instructions, cause the apparatus to at least: receive an indication of a plurality of articles to be stored in a tray; determine a plurality of bins corresponding to the plurality of articles; generate a layout of the plurality of bins on the tray; identify locations of the plurality of articles within the plurality of bins on the tray; and cause the tray to be configured according to the layout of the plurality of bins on the tray.

DESCRIPTION OF THE DRAWINGS

Reference now will be made to the accompanying drawings, which are not necessarily drawn to scale, and wherein.

DETAILED DESCRIPTION

Figure 1:
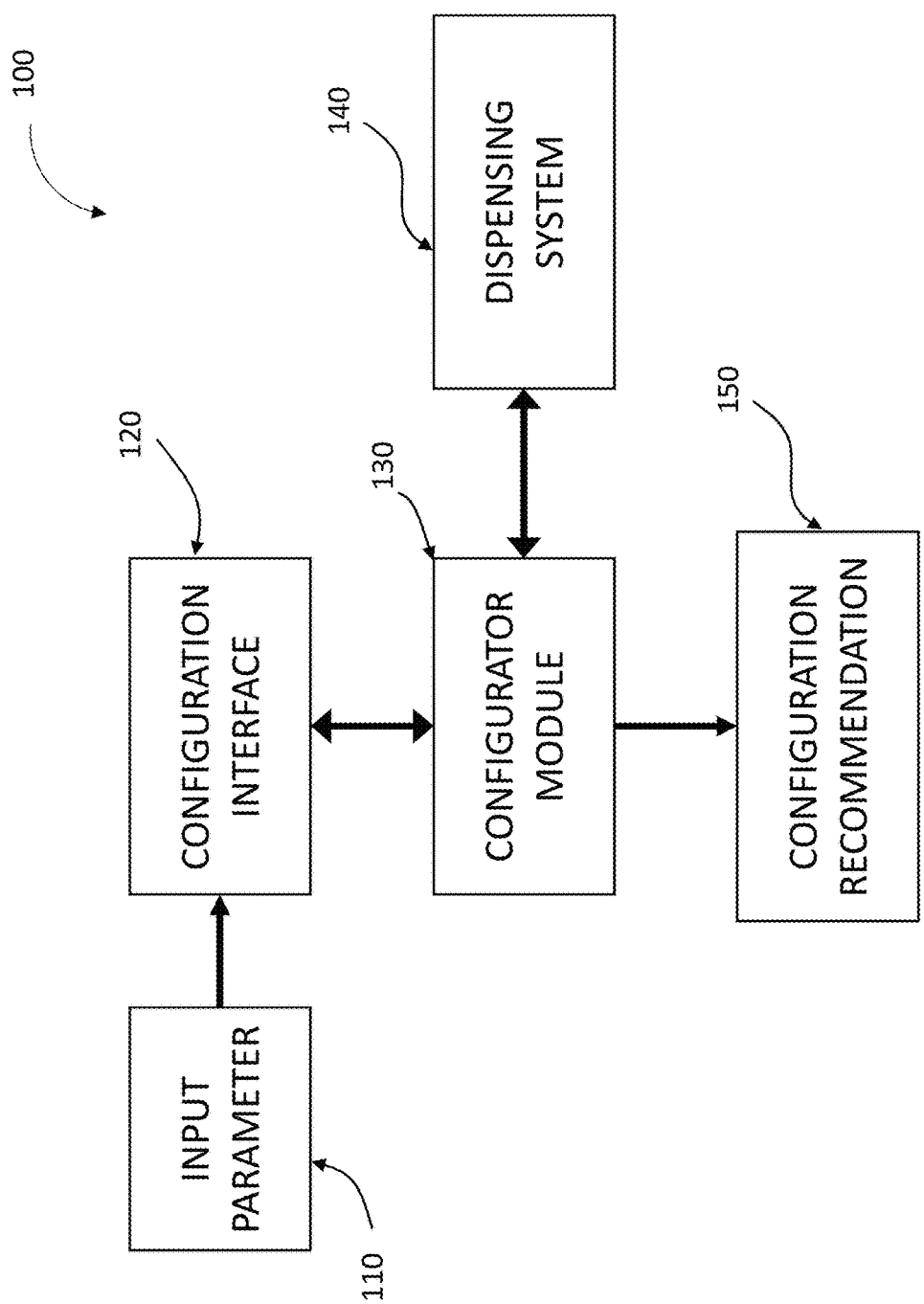
FIG. 1 is a block diagram of system for configuring a tray of a dispensing system according to an example embodiment of the present disclosure.

Embodiments of the present invention may provide various apparatuses, systems, and methods for improving the efficiency of medication distribution within a healthcare facility. Some embodiments and components of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements.

Example embodiments of the present disclosure may provide a method, apparatus, and computer program product which may facilitate storage, tracking, and dispensing of articles. Embodiments improve the accuracy and efficiency with which articles may be stored, tracked, and dispensed through user-configurable storage means and automated configuration of storage means. Embodiments may incorporate mechanisms that solve issues identified by the applicant as substantial hurdles in automating the storage, tracking, and dispensing of articles, particularly when those articles are of differing sizes, shapes, and weights.

While storage, tracking, and dispensing systems of example embodiments described herein may be used to dispense various types of articles, the primary embodiment described herein is particularly well suited for dispensing articles of various sizes and shapes through user or automated configuration and optimization of storage trays.

Embodiments described herein may be suitable for use with any industry in which storage, tracking, and dispensing of articles is necessary. Embodiments may be particularly well suited to the storage, tracking, and dispensing of medications as will be evident from the disclosure below. While certain aspects of embodiments described herein may be specific to medication or medical supply dispensing and the associated accuracy required therewith, similar implementations may omit certain features or include other features as would be apparent to one of ordinary skill in the art.

Embodiments of customized, configurable storage trays may be employed in both automated storage/dispensing and manual storage dispensing. In the medical field, manual storage and dispensing may take the form of nurse carts or crash carts, for example, where a cart is stocked with medications and supplies of various sizes and form factors to accommodate various scenarios where the contents may vary facility to facility and season to season. Automated storage and dispensing in the medical field may take the form of an automated medication dispensing system. Whether it is manual storage/dispensing or automated storage/dispensing, the articles stored and dispensed may be of a variety of form factors from individual pills or capsules to intravenous bags of up to a liter in capacity. Other form factors may include syringes, carpujects, vials, multi-dose medication containers, etc. Supplies, such as intravenous medication tubing, empty syringes, etc. may also be stored and dispensed from manual or automated systems. Both the supplies and the medications may come in a variety of sizes and shapes and may not be easily and efficiently dispensed from a conventional automated dispensing apparatus or efficiently stored in a manual storage and dispensing system of a standard configuration.

Embodiments described herein may be employed in automated dispensing systems, semi-automated dispensing systems, or manual dispensing systems as will be appreciated by one of ordinary skill in the art. Automated dispensing systems, as described herein, require an inventory of articles to be dispensed upon receiving or processing a request for an inventory article. Automated dispensing generally involves the retrieval of an article using robotic means, such as a multi-axis arm with an end-of-arm-tool to retrieve and dispense an article. Semi-automated dispensing systems may involve some automation, such as guiding a user to a location and identifying the article to be retrieved by the user for dispensing. Manual dispensing systems may rely on a user finding an article and dispensing the article with minimal assistance. The configurable trays of example embodiments described herein may be employed in any of these dispensing systems.

In accordance with one embodiment of the present solution, a configuration tool 100 for a dispensing system is illustrated in FIG. 1. The configuration tool 100 includes provisions to receive user input 110 at a configuration interface 120. The user input can be in a variety of forms. For example, when the user is stocking items such as unit doses of medication, the user input may include information such as medication type, medication size, medication form, item volume, medication weight, etc. The variety of the information is provided for illustrative purposes only. Any information that will help understand the characteristics of the item (medication, in this case) may be considered as permissible. When more than one item is being considered, then the configuration interface 120 will receive user input about characteristics of each of the one or more items.

The user input 110 received at the configuration interface 120 is then delivered to the configurator module 130 where it is processed to determine a recommended layout (not currently shown) that a user may consider while arranging the one or more items. In certain aspects of the present technique, the arrangement of the one or more items may be performed on a tray (not currently shown). In typical cases, arrangement of the one or more articles may involve the use of separators or boundary elements. One or more boundary elements may be utilized to represent a storage area or cavity. This in some cases may resemble a bin. The sizing of such storage areas, whose boundaries may be defined by one or more separators, may be determined by the configurator module based on the characteristics of the one or more articles. A tray may include at least one such storage area. In typical cases, where more than one article is required to be stored within the tray, more separators may be utilized to define more than one storage area. In some examples, two adjacent storage areas may share a common separator. However, it is also possible for two separate storage areas to not have a common separator. A tray formed with such storage areas or cavities may then be stocked with the one or more items and advantageously loaded into the dispensing system. Storage of the one or more articles/items may be made in groups determined by either the type of the article, or shape of the article, or by the intended recipient, such as an end user (example: patient). The choice of the separators used to define the storage areas may be made based on the size of the one or more items such that all the items may be safely and securely stored. It may be advantageous to store the one or more items in groups. In one exemplary embodiment, all medications classified as 'painkillers' may be stored in one storage area. In another exemplary embodiment, all medications classified as 'IBUPROFEN 200 mg' may be stored in a single storage area regardless of the brand or the manufacturer. In another exemplary embodiment, all medications classified as 'ADVIL' (as an example) which is a particular brand of Ibuprofen made by Pfizer may be stored in a single storage area. It must also be apparent to a person skilled in the art that that you can have different forms of an item, such as a medication from different manufacturers in the same location as long as the medications are clinically the same.

In some instances, the arrangement of the one or more items may require more than one tray, driven essentially by the quantity of the one or more items but in some other cases also by size, volume or weight. In such cases, the configurator module 130 may be considered as being able to provide instructions on how much of each of the one or more items must be placed in tray 1, tray 2, etc. until all of the required one or more items are fully arranged in one or more trays. It must also be appreciated that the configurator module 130 provides a suggested layout in the form of a configuration recommendation 150 to the user. The user may advantageously use the recommendation 150 to efficiently arrange the one or more items prior to loading into the dispensing system. The recommendation 150 may be provided in the form of an electronic display, or in a printable format. In some cases, the system 100 may include a display device (not currently shown) to display the recommendation. In some other cases, the system 100 may also have capability to verify if the actual prepared layout is the same as the recommended layout in the form of the configuration recommendation 150.

Figure 2:
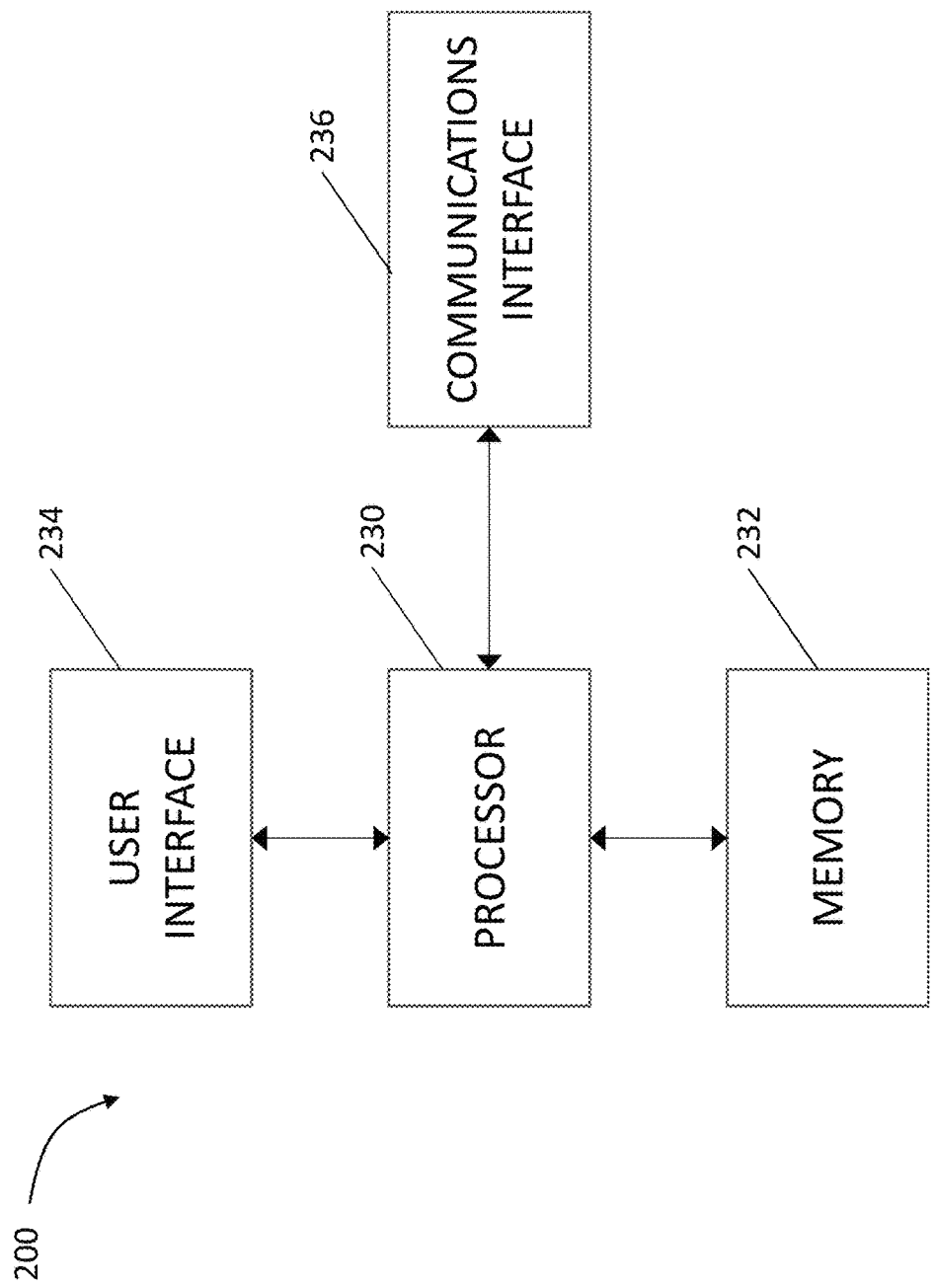
FIG. 2 is a block diagram of an example apparatus which may be implemented as a controller according to an example embodiment of the present disclosure.

Automated and semi-automated dispensing systems may require a controller configured to control the functions of the automated dispensing. The controller may be configured in a variety of manners, an example of which is illustrated in FIG. 2. The controller of example embodiments may include processing circuitry. The processing circuitry may be configured to perform actions in accordance with one or more example embodiments disclosed herein. In this regard, the processing circuitry may be configured to perform and/or control performance of one or more functionalities of the handling, storing, or distributing of articles such as medications and/or supplies in accordance with various example embodiments. The processing circuitry may be configured to perform data processing, application execution, and/or other processing and management services according to one or more example embodiments. In some embodiments, a computing device or a portion(s) or component(s) thereof, such as the processing circuitry, may be embodied as or comprise a circuit chip. The circuit chip may constitute means for performing one or more operations for providing the functionalities described herein.

A schematic illustration of an apparatus which may be implemented as a controller of an automated or semi-automated dispensing system 200 is illustrated in FIG. 2. The controller of the dispensing system 200 may be embodied as the configurator module 130 of FIG. 1, or may be a separate entity embodied as part of the dispensing system 140. As shown, in some example embodiments, the processing circuitry may include a processor 230 and, in some embodiments, may further include memory 232. The processing circuitry may be in communication with, include or otherwise control a user interface 234 and/or a communication interface 236. As such, the processing circuitry may be embodied as a circuit chip (e.g., an integrated circuit chip) configured (e.g., with hardware, software, or a combination of hardware and software) to perform operations described herein.

The processor 230 may be embodied in a number of different ways. For example, the processor may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor may comprise a plurality of processors. The plurality of processors may be in operative communication with each other and may be collectively configured to perform one or more functionalities of a system for handling, storing, transporting, or distributing medication as described herein. The plurality of processors may be embodied on a single computing device or distributed across a plurality of computing devices. In some example embodiments, the processor may be configured to execute instructions stored in the memory or otherwise accessible to the processor. As such, whether configured by hardware or by a combination of hardware and software, the processor may represent an entity (e.g., physically embodied in circuitry—in the form of processing circuitry) capable of performing operations according to embodiments of the present invention while configured accordingly. Thus, for example, when the processor is embodied as an ASIC, FPGA, or the like, the processor may be specifically configured hardware for conducting the operations described herein. Alternatively, as another example, when the processor is embodied as an executor of software instructions, the instructions may specifically configure the processor to perform one or more operations described herein.

In some example embodiments, the memory 232 may include one or more non-transitory memory devices such as, for example, volatile and/or non-volatile memory that may be either fixed or removable. In this regard, the memory 232 may comprise a non-transitory computer-readable storage medium. It will be appreciated that while the memory 232 is illustrated as a single memory, the memory may comprise a plurality of memories. The plurality of memories may be embodied on a single computing device or may be distributed across a plurality of computing devices. The memory may be configured to store information, data, applications, instructions and/or the like for enabling embodiments of the present invention to carry out various functions in accordance with one or more example embodiments. For example, the memory may be configured to buffer input data for processing by the processor. Additionally or alternatively, the memory may be configured to store instructions for execution by the processor. As yet another alternative, the memory may include one or more databases that may store a variety of files, contents, or data sets. Among the contents of the memory, applications may be stored for execution by the processor to carry out the functionality associated with each respective application.

A user interface 234 of example embodiments, such as the user interface of a user module of an automated dispensing system, may be in communication with the processing circuitry to receive an indication of a user input at the user interface and/or to provide an audible, visual, mechanical, or other output to the user. As such, the user interface may include, for example, a user input interface 234 such as a keyboard, a mouse, a joystick, a display, a touch screen display, a microphone, a speaker, and/or other input/output mechanisms. As such, the user interface 234 may, in some example embodiments, provide means for user control of embodiments of the present invention. In some example embodiments in which the invention is embodied as a server, cloud computing system, or the like, aspects of the user interface may be limited or the user interface may not be present. In some example embodiments, one or more aspects of the user interface may be implemented on a user terminal. Accordingly, regardless of implementation, the user interface may provide input and output means to facilitate handling, storing, transporting, or delivery of medication in accordance with one or more example embodiments.

The communication interface 236 may include one or more interface mechanisms for enabling communication with other devices and/or networks. In some cases, the communication interface may be any means such as a device or circuitry embodied in either hardware, or a combination of hardware and software that is configured to receive and/or transmit data from/to a network and/or any other device or module in communication with the processing circuitry. By way of example, the communication interface 236 may be configured to enable embodiments of the present invention to communicate with application server(s) and/or networks and/or information databases. Accordingly, the communication interface may, for example, include supporting hardware and/or software for enabling communications via cable, digital subscriber line (DSL), universal serial bus (USB), Ethernet, or other methods.

Figure 3:
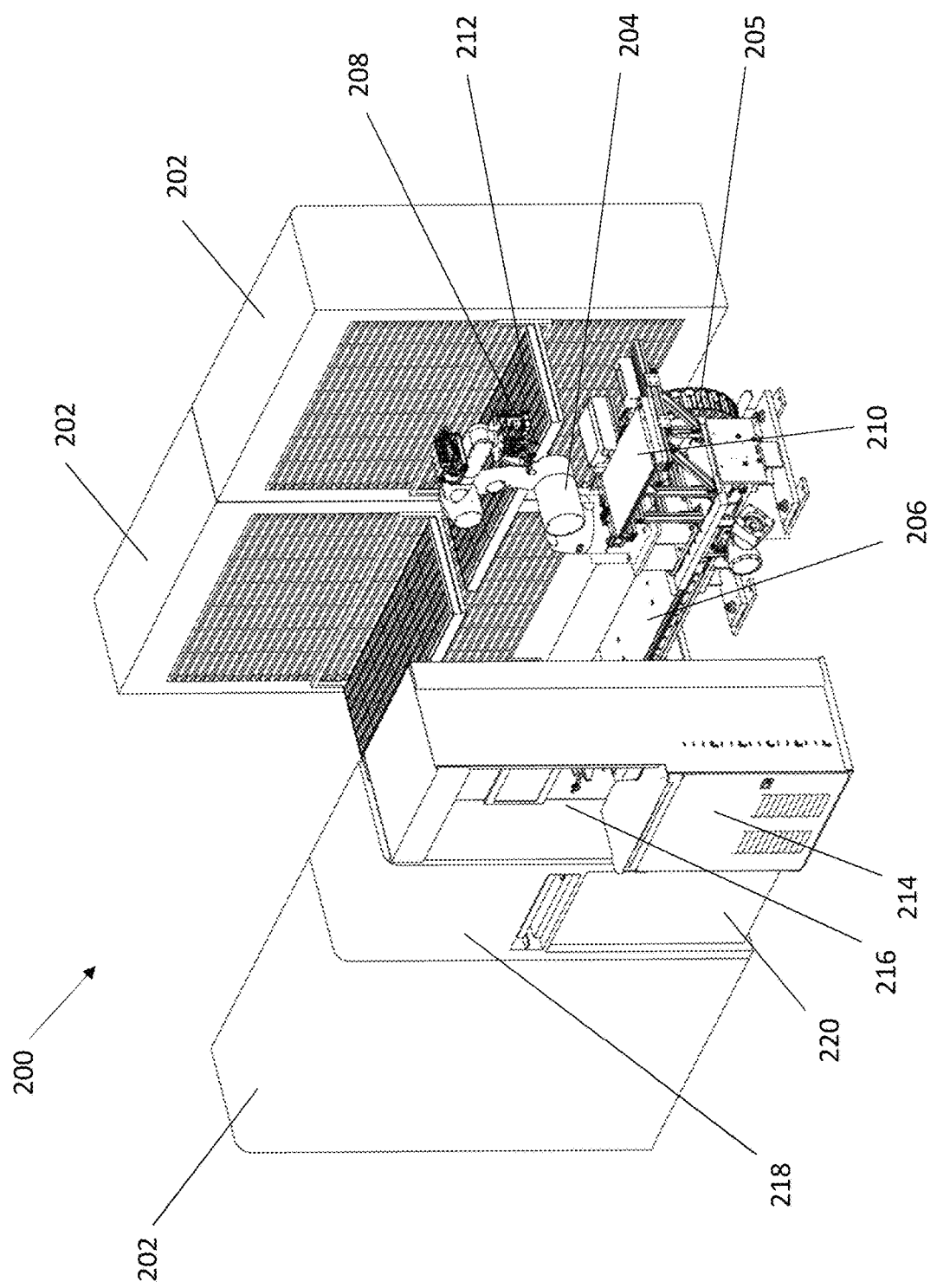
FIG. 3 is an example embodiment of an automated dispensing system according to an example embodiment of the present disclosure.

FIG. 3 illustrates an embodiment of an automated dispensing system 200 according to an example embodiment of the present disclosure which may be controlled by a controller as described above with respect to FIG. 2. The illustrated embodiment includes a plurality of storage modules 202 arranged proximate a robot 204, which may be, for example, a multi-axis robotic arm for retrieval and dispensing of articles as described further below. The robot 204 may be positioned on a track system 206 to allow the robot to move along the track providing greater access to the storage modules and allowing for expandability and modularity of the automated dispensing system. The robot 204 may include an end-of-arm tool 208 configured to attach to articles for retrieval, movement, and placement as necessary. While example embodiments described herein employ a robot 204 positioned on the track system 206, embodiments may include a robot that is either stationary and in a fixed location, or optionally, a robot that is free to move between modules described herein through some form of self-propulsion.

According to some embodiments, a work platform 210 may be provided to facilitate distribution of articles and the manipulation of articles as will be evident by the following disclosure. This work platform 210 may advantageously be coupled to the robot 204 and may traverse the track system 206 with the robot 204. The robot and work platform 210 may move along the track system in any conventional manner, such as with a pinion gear attached to the robot 204 base, with a rack gear extending along the track system. Optionally, the robot 204 may be belt-driven along the track system 206. Regardless of the motive mechanism of the robot along the track system, the position of the robot along the track system may be precisely monitored via embedded sensors or tags in the track system, displacement measurement of the robot 204, or any method of measuring a position along the track system accurately. The measurement of position along the track system 206 may facilitate accurate and repeatable movement of the robot 204 arm and positioning of the end-of-arm tool 208 to enhance accuracy of retrieval and movement of articles throughout the system 200. Electrical power, hydraulic power (if needed), pneumatic communication (e.g., vacuum or pressure), and hard-wired communications may be in communication with the robot 204 through an umbilical 205 or multiple umbilicals which may bundle all necessary wiring, plumbing, etc. and may enable the robot 204 to traverse the track 206 while remaining in electrical and fluid communication with stationary equipment, such as a controller, hydraulic pump, pneumatic pump, and electrical power source, for example.

The storage modules 202 may be configured to store a plurality of articles, where each article is accessible to the end-of-arm tool 208 of the robot 204. While an arrangement of vertical shelves may be sufficient to store a plurality of articles, in order to increase the storage density, the available storage locations may extend horizontally to provide a substantial increase in storage capacity. To achieve this increased storage capacity, the storage modules may include a plurality of trays 212 which may be received within the storage modules 202 and may be configured to be moved between a storage position where the tray 202 is received within the storage module, and a retrieval position, in which the tray 212 is slid out from the storage module, accessible to the robot 204 and end-of-arm tool 208. These trays may be custom configured as detailed further below.

The automated dispensing system 200 of example embodiments may further include a user module 214, which may be embodied by the controller of FIG. 2, or separate therefrom. While an automated dispensing system 200 of example embodiments may be capable of being fully controlled through a remote interface or remote order request/ fulfillment apparatus, such as a remote workstation, computer, controller, etc., the illustrated embodiment includes a user module 214 integrated with the automated dispensing system. The user module 214 may include a user interface 216. The user interface 216 may include a means for providing information to a user, such as a display (e.g., light emitting diode (LED) display, organic LED display, liquid crystal display (LCD), plasma display, etc.), and a means for a user to provide information. The means for providing information may include a touch screen display, a keyboard, pointing device (e.g., mouse), a scanning device (e.g., barcode scanner or radio frequency identification (RFID) scanner, etc.), or the like. The user module 214 may be used to request the dispensing of articles, to review a queue of articles to be dispensed, to review errors or correct issues, etc.

The automated dispensing system 200 of example embodiments may retrieve and dispense articles in an automated manner, and may do so to a delivery device. For example, the automated dispensing system 200 may dispense articles from the trays 212 to, for example, a bin. According to an example embodiment of an automated dispensing system of a healthcare facility, the system may receive a request to dispense one or more medications for a particular patient. In response, the robot 204 may advance along the track system 206 to a position for accessing a tray containing one or more of the requested medications. The tray 212 may be advanced to the retrieval position, either through a mechanism of the storage module 202, or using the robot 204 to move the tray to the retrieval position. Once the tray is in the retrieval position, the robot end-of-arm tool 208 may be moved by the robot 204 to a position above the location in the tray where one of the requested medications is stored. The end-of-arm tool 208 may retrieve the medication stored therein, and move the medication to a dispensing location. The dispensing location may be, for example, a patient-specific bin, which may be positioned on the work platform 210, or may be positioned at a dispensing area of a module of the automated dispensing system 200. Once the requested medications for the patient have each been retrieved and dispensed to the patient-specific bin, the bin may be moved to a location for transport to the patient. One such example of a transport device is a cart, such as a nurse cart.

The illustrated embodiment of FIG. 3 includes a cart module 218 and a cart 220. The cart 220 may be embodied as a replenishment cart including a plurality of trays which may be customized according to example embodiments described herein, or may include a nurse cart or crash cart, for example. A nurse cart or crash cart may receive articles dispensed by the automated dispensing system to stock or replenish the cart. The cart may receive dispensed articles in one or more trays of the cart which may be customized as described further below. Additionally or alternatively, the automated dispensing system 200 may be configured to swap out customized trays to provide a tray with a configuration that is more appropriate for the articles to be dispensed to the cart. Optionally, customized trays may be preconfigured and pre-stocked with articles, particularly when the pre-stocked tray is stocked with articles common to a specific purpose and used frequently in the facility.

An example of a cart, whether a replenishment cart, nurse cart, crash cart, or the like, may be received within the cart module 218 from a position outside of the automated dispensing system 200, such that movement of the cart into and out of the cart module may not disrupt the operation of the robot 204 within the system. The cart may be accessible within the cart module 218 to the robot 204. The robot may move the articles such as medications or pre-stocked trays to the cart 220 of the cart module 218 such that the articles are dispensed to a tray on the cart or a stocked tray is inserted into the cart 220.

Figure 4:
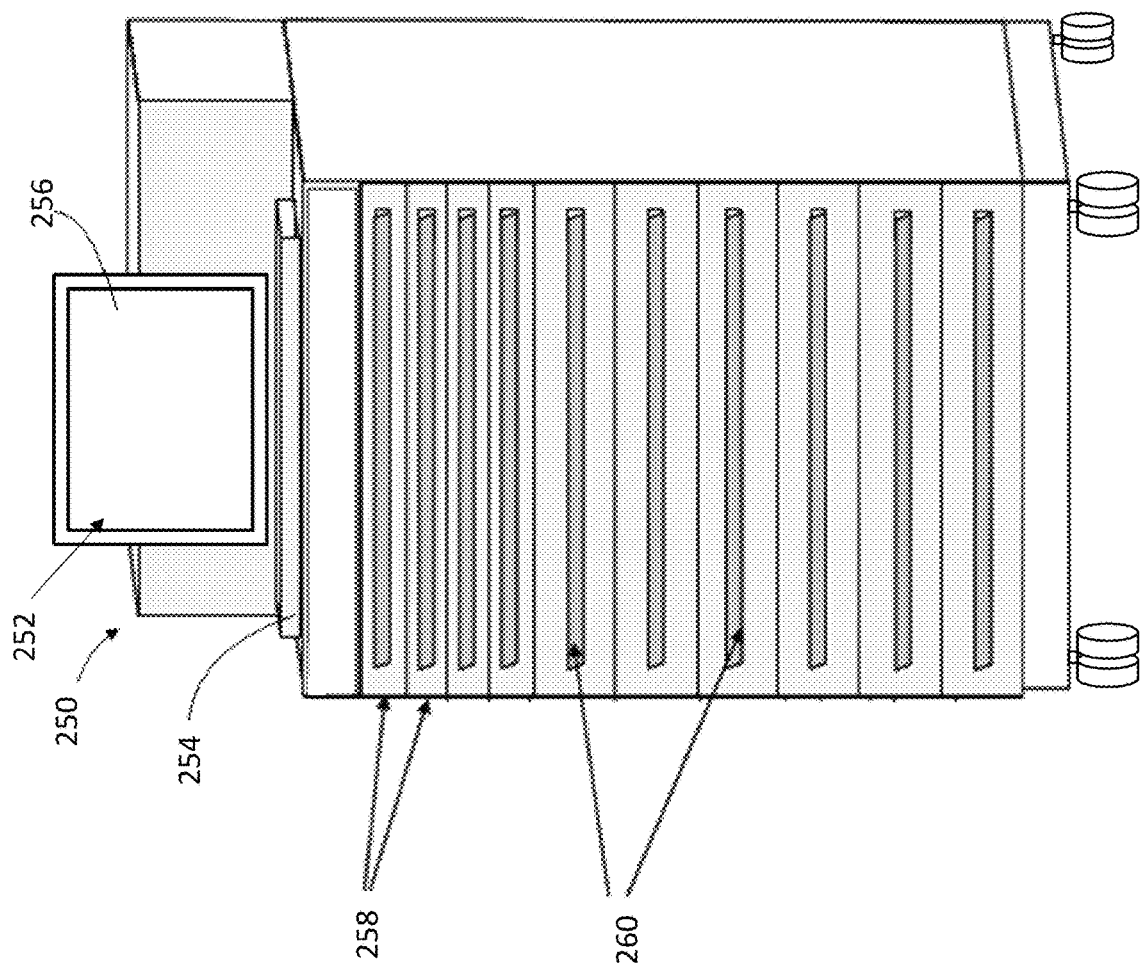
FIG. 4 is an example embodiment of a nurse cart which may employ embodiments of the present disclosure.

According to example embodiments described herein, the automated dispensing system 200 may dispense a plurality of articles, such as medications, to a transport device, such as a cart 220, without requiring manual intervention. This automated dispensing may be achieved through proper identification of articles as they are received in the automated dispensing system 200 and as they are retrieved within the system for dispensing. An example embodiment of a cart 250 is illustrated in FIG. 4, which may be a nurse cart. As shown, the cart 250 may include a work station 252, which may be embodied by the apparatus of FIG. 2 and may include processing circuitry, a user interface, communications interface, memory, etc. The user interface may include a keyboard 254, mouse, touch screen, track ball, etc. capable of entering information or selecting options shown on the display 256. The cart 250 may include a plurality of drawers or sliding trays 258, 260 configured to hold articles. The trays may include different heights to accommodate different sizes of articles, such as shorter trays 258 and taller trays 260.

In order to provide accessible, organized storage for articles in a dispensing device, whether it is the automated dispensing system 200 of FIG. 3 or a nurse cart 250 of FIG. 4, trays are used to present articles for retrieval by a user or by automated, robotic means. Conventionally, trays have one or more defined storage areas, with dividers between storage areas to separate contents of a tray as needed. However, these defined storage areas may not be well suited for efficient storage of articles of varying sizes and shapes when a variety of articles are stored in a single tray. For example, referring again to the medical field, a tray may be used to store both unit dose blisters of medications which may be very small and intravenous bags which can be very large. While a tray may be configured with both large and small storage areas, the quantities of differently sized and shaped articles may vary from tray to tray such that no fixed tray configuration is useful in all scenarios.

Embodiments provided herein enable a single tray to be configured to accommodate a user-defined mix of articles of different sizes and shapes to increase, such as to maximize the efficiency of storage in a tray. Trays may be configured for a variety of purposes and scenarios and trays may be re-configured as needed with changing needs.

While embodiments of the present disclosure may be employed in any of a variety of industries, an example embodiment is described herein with respect to the medical field. The medical field employs fulfillment and dispensing of articles in a variety of manners and in a variety of different types of care facilities such that no two dispensing operations may be the same. Pharmacy technicians, nurses, and automated dispensing devices may populate trays for nurse carts, crash carts, offline storage trays, etc. with non-homogeneous drugs and supplies to suit the individual needs of a facility and even differing needs within different areas of a single facility. Embodiments of the present disclosure create customizable trays using automation to uniquely serve these needs.

An original equipment manufacturer of a nurse cart or crash cart may not accommodate specific tray types for the needs of a specific facility or preferences of an individual such that the trays are often filled by hand in an inefficient manner where space within the tray is not optimized. Further, articles may not have unique storage locations such that they may be comingled with other articles placing greater burden on a nurse or doctor to search among comingled articles to retrieve the article for which they are searching.

Figure 5:
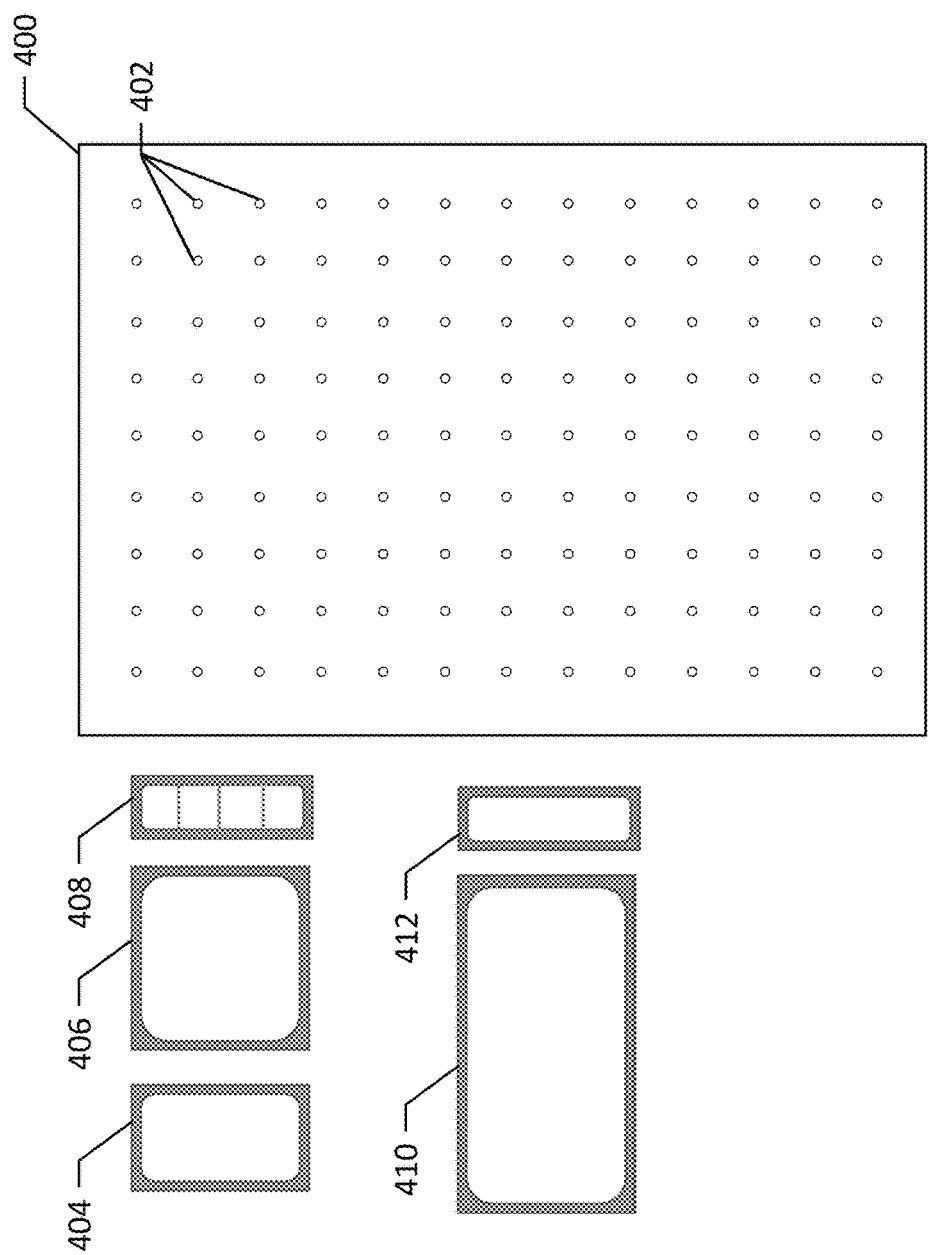
FIG. 5 is a tray and a plurality of configurable bins according to an example embodiment of the present disclosure.

According to embodiments described herein, customized trays may be created that specifically accommodate the needs of a user and which can be changed as needs of a user change. FIG. 5 illustrates an example embodiment of a customizable tray 400 which may include a series of holes 402 or detents into which bins of various shapes and sizes may be received. While FIG. 5 illustrates a series of holes 402, embodiments may include a variety of attachment means to secure the configurable bins to the tray, such as magnets, pegs/pins, suction cups, clips, Velcro as well as any other custom mating geometry that will allow an attachment between the bin (including nests, bins and separators) and the tray, etc. Also shown in FIG. 5 are a plurality of different sized bins 404, 406, 408, 410, 412. Bins, such as bins 404, 406, 410, and 412 may include a single compartment, while bins such as bin 408 may include a plurality of smaller compartments. Bins may be of any appropriate size and shape and may be customized based on the articles to be stored and dispensed in trays for different purposes.

As discussed earlier, bins 404, 406, 408, 410 and 412 as shown in FIG. 5 may be pre-formed, or be formed using sub-components (not currently shown) that involve the use of separators for forming one or more sides of the bins. The advantage of such a feature includes the ability to customize the size of the bin to accurately fit items that are not of standard dimensions, or include non-standard items. The use of the word bin in this document should be construed as including pre-formed bins of fixed shapes, sizes and depth, as well as the ability to custom-form a bin using separators. Furthermore, as an example, to form a custom bin to resemble bin 408, we may require the use of multiple separators to form the outer boundary and one or more dividers to form the inner boundary. Each of the separator may be secured to the tray using one or more holes 402. In some embodiments, separators may include provisions for securing the dividers i.e., dividers may not always be attached to the holes 402 but rather they may be attached to the separators.

Figure 6:
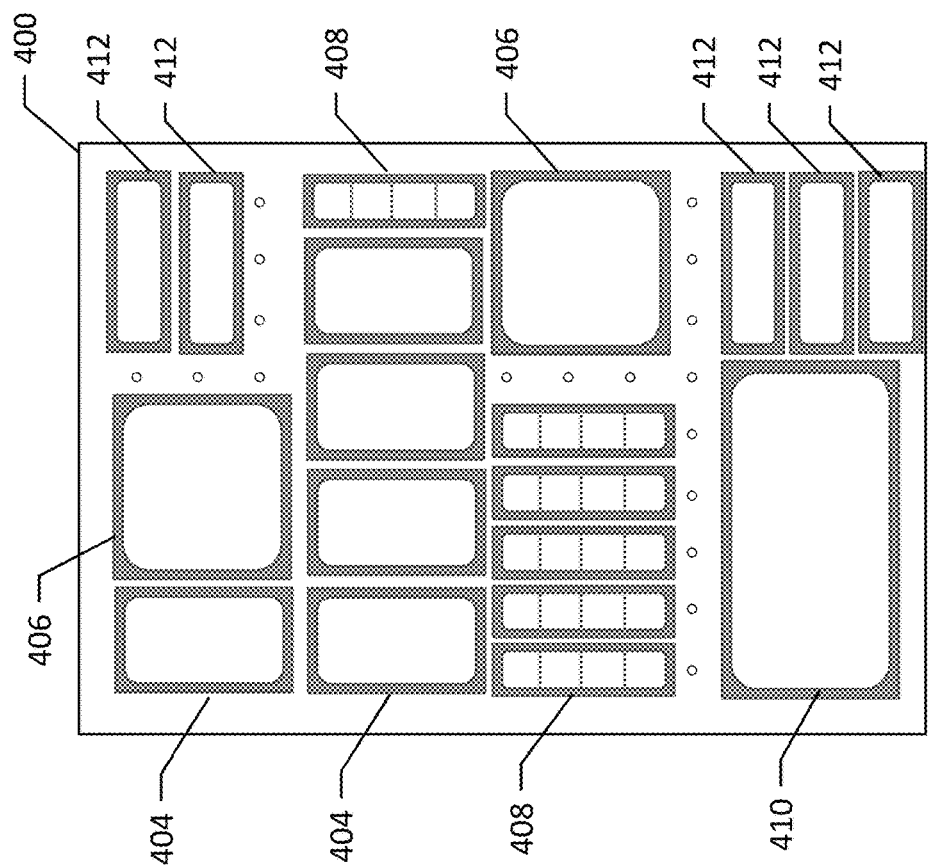
FIG. 6 is a tray with a plurality of bins arranged on the tray according to an example embodiment of the present disclosure.

Using the attachment means to secure the bins to the tray, such as the holes 402 of tray 400, the bins may be secured to form a tray with a customized layout of bins of various sizes and shapes as illustrated in FIG. 6. As shown, the various bin sizes depicted in FIG. 5 are positioned on the tray 400 and secured to the tray using the attachment means of holes 402. The bins may include mating attachment means such as pins to be received within the holes 402. Using alternative attachment means may include magnets on the bins attaching the bins to a magnetic or ferrous metal substrate, bins received within clips of the tray 400, bins with holes configured to receive pins extending from the tray, or any means available to secure the bins to the tray in a manner that keeps the bins in a secure position while the tray may be moved. It is also envisioned that in some exemplary embodiments, the mechanical affixation of a nest, bin or separator(s) to a tray may also trigger an electric/electronic signal caused by the mechanical affixation. Such electrical/electronic signals may be utilized to additionally detect the affixation as well as confirm the position of the affixation. This may serve as primary or secondary means to confirm the position, arrangement and/or orientation of the nest, bin or separator.

According to an example embodiment, the bins 404, 406, 408, 410, and 412 may include identifiers of the type or size of bin, where the identifier may be a radio frequency identifier (RFID) or barcode identifier. The bin identifier may be read upon installation on the tray 400, such as using an RFID reader associated with the tray to identify the location in which the identified bin was installed. Optionally, the pin configuration or other mechanism for attaching the respective bin to the tray 400 may be unique for each bin size such that the tray may recognize a bin type/size/shape based upon the engagement with the tray.

Using the customizable configuration of bins, embodiments may provide customized trays for any purpose in which such storage and dispensing is appropriate. The manner in which the bins are arranged on the tray and the sizes of bins selected may be automated or semi-automated as described herein. Further, trays may be reconfigured as needed when the needs of a user change and articles of different sizes, shapes, or quantities are needed.

Figure 7:
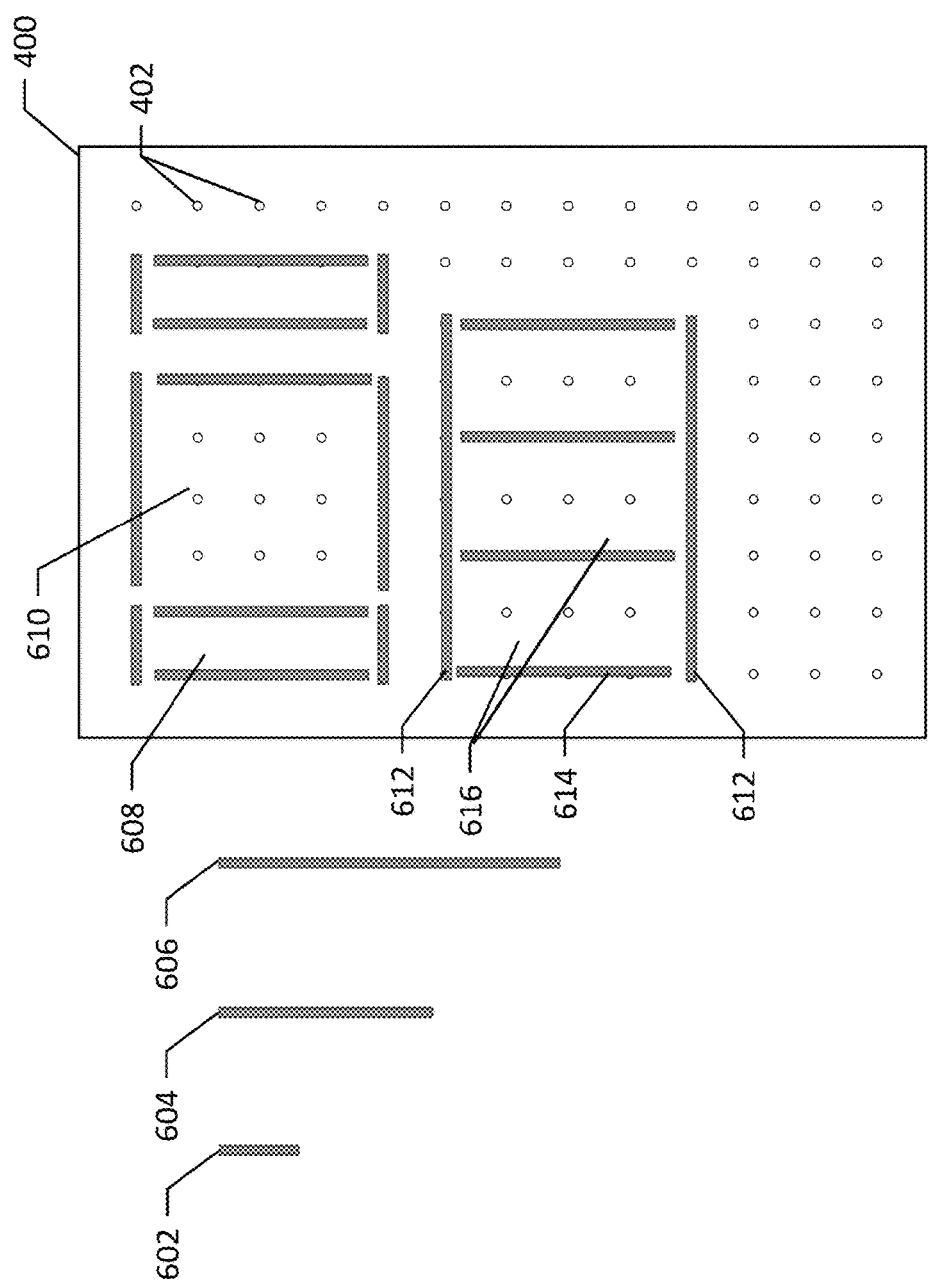
FIG. 7 is a tray and a plurality of configurable separators according to an example embodiment of the present disclosure.

While FIGS. 5 and 6 depict differently sized bins that may be used to customize and configure a tray 400, FIG. 7 illustrates another embodiment in which separators or separators of various sizes are used to define the boundaries of a bin or the storage areas within the bins. As shown, separators may be of various sizes, such as short separator 602, medium separator 604, and long separator 606. While three separator sizes are shown, any number of separators may be used. The separators may be placed on the tray 400 using attachment means to form bins such as bin 608 and bin 610. Separators may be shared by more than one bin, such as long separators 612 used in combination with medium separators 614 used to define several bins 616. Further, separators may be of a flexible material such that they can be curved to provide more than one side to a bin of a tray. Thus, as described herein, bins may be formed within a tray using either pre-formed bins or custom-formed bins using one or more separators as illustrated. In some instances, the separators may be used to create spaces that aren't just defined by a length and a breadth but also by height.

Figure 8:
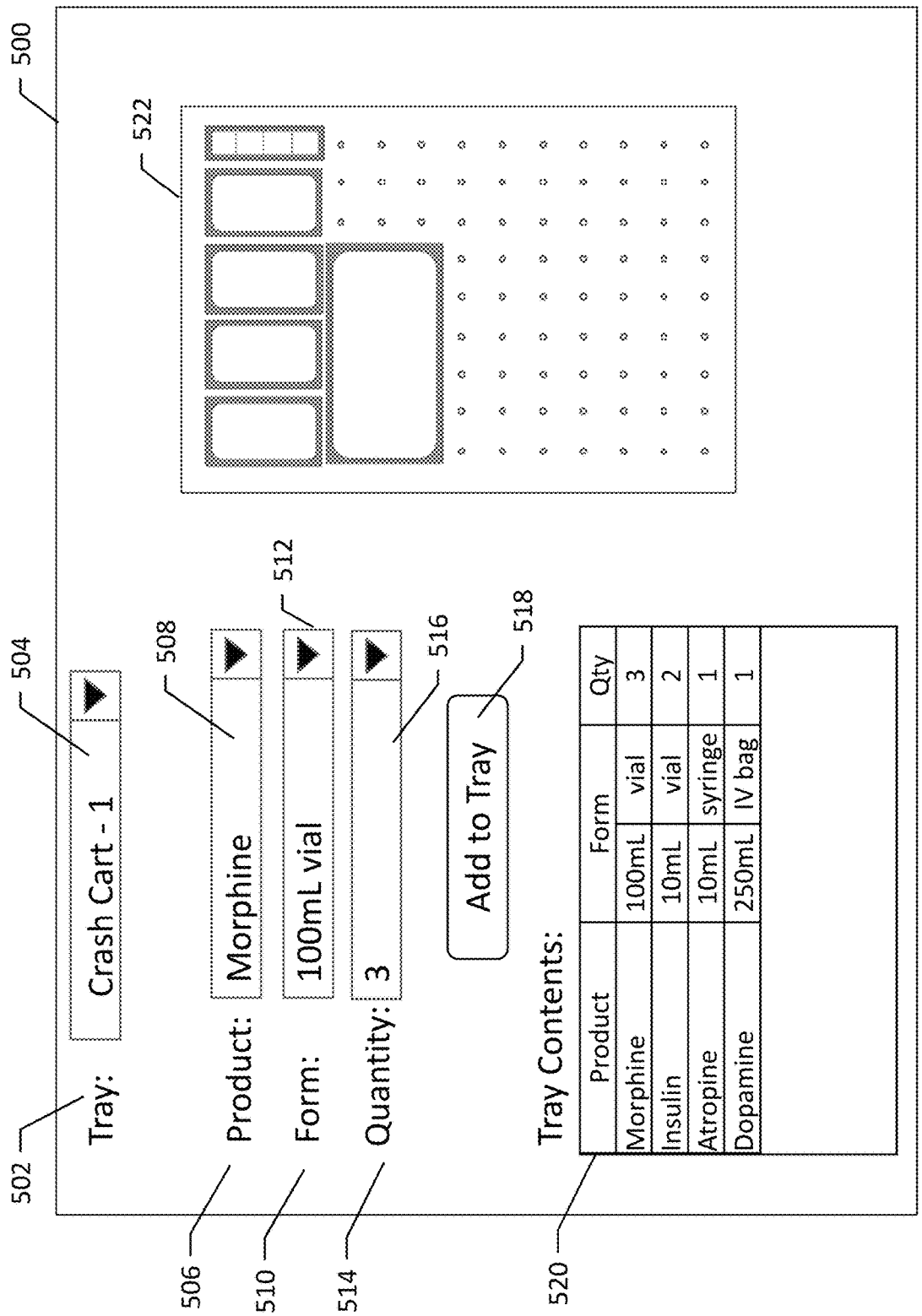
FIG. 8 illustrates a tray configurator user interface according to an example embodiment of the present disclosure.

According to an example embodiment, a user may determine what articles are to be stored within a tray through selection of articles, such as on a user interface (e.g., user interface 234 of FIG. 2). FIG. 8 illustrates an example embodiment of a user interface 500 in which contents of a tray are selected in order to populate the tray with the appropriately sized bins or bin areas. As illustrated, a tray 502 is selected for configuration using drop down menu 504, which in the illustrated embodiment shows tray number one of a crash cart. A product 506 is selected in dropdown menu 508, with a form 510 through menu 512, and a quantity 514 through drop down menu 516. Once selected, the contents may be added to the tray inventory through the "add to tray" button 518. The current tray contents are shown in window 520, while a physical tray layout is illustrated at 522. A bin of appropriate size may be selected by the software to contain the different elements of the content. While each individual item of the tray contents may be designated for separate bins, embodiments may enable a user to store multiples of a particular product in a single bin, such as multiple unit dose blisters of a medication in a single bin within the tray.

The software for configuring the tray layout 522 of FIG. 8 may include space optimization software which may optimize the layout of the tray based on the sizes of bins needed to contain the tray contents 520. Optionally, if a tray is being stocked and customized for a multi-tray cart, the software may be configured to optimize the layout of contents of several trays across several trays providing more flexibility for the software to optimize space among the trays. However, in an example embodiment in which a single tray is being configured, the software may optimize the single tray based on the desired contents of that tray, and inform a user when the tray is over capacity and how the user may remove one or more items to be within the storage capacity of the single tray.

Figure 9:
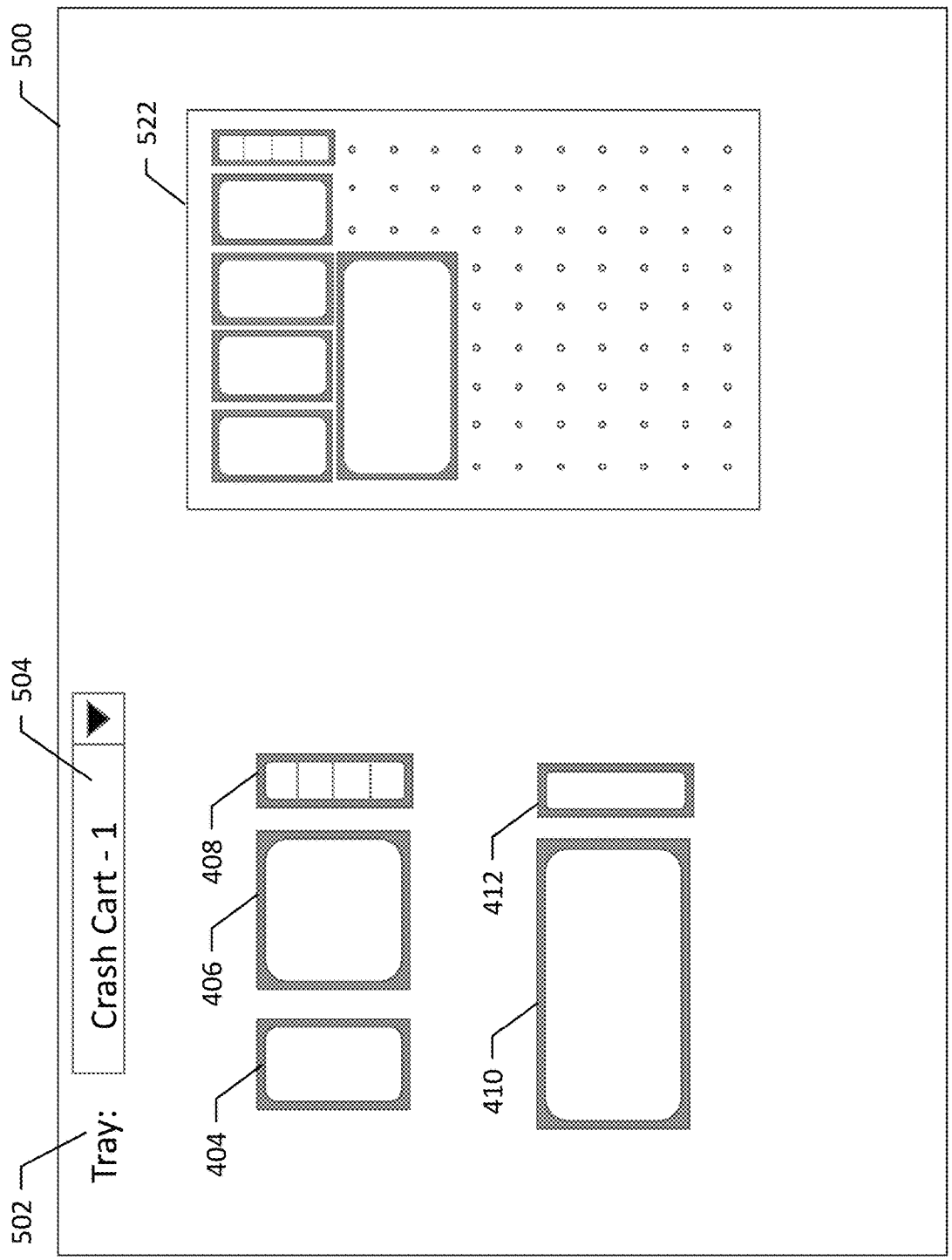
FIG. 9 illustrates another tray configurator user interface according to an example embodiment of the present disclosure.

According to some embodiments, a user may build a tray virtually using building blocks of bins/separators as shown in FIG. 9 where a user may select a specific configuration and place one or more separators/pre-sized bin layouts on the layout of the tray 522. This may be a drag-and-drop operation where a user drags a selected separator or bin to the layout of the tray 522. The separators/bins may visually appear to "snap" into position closest to where the user drops the separator/bin to better align the bins with the tray. Alternatively, a user may simply drag separators/bins to the layout of the tray 522, and the software may re-configure the layout of the tray 522 to optimize the layout of the selected separators/bins.

While a tray layout may be generated using the user interface described with respect to FIGS. 7 and 8, embodiments may assemble the trays with the separators/bins in the designated locations either manually or in an automated manner. The layout of the tray 522 identified through the software may provide a map by which a user selects bins from a plurality of storage of bins, and assemble those selected bins to the tray as instructed by the layout. Optionally, a tray may be assembled through automated means whereby a robot selects the separators/bins identified in the layout and deposits the bins on a tray as identified. An automated dispensing system, such as the system 200 of FIG. 3, may be capable of building such customized trays on an as-needed basis.

A semi-automated mechanism for physically building a tray layout may include automated dispensing of the appropriate separators/bins for an identified tray layout where the user builds the layout according to the identified layout. A tray layout may be monitored by an image capture device which may confirm that bins are appropriately placed in the locations identified in the layout, and may alert a user if a bin is misplaced or if a bin of an inappropriate size is used in a particular position. This may assist a user in building a tray commensurate with the tray identified in the software.

Optionally, a light source may be used to project onto a tray the locations for each of the plurality of bins on the tray such that a user may build the tray based on the projected layout on the tray. This projected layout may aid a user in identifying the appropriate attachment means for a bin or a separator rather than relying on the user counting holes or pins to confirm the appropriate location for a bin or separator.

In accordance with another aspect of the present invention, a user may form a tray layout using an initial set of separators/bins. This tray layout may be advantageously be improved or optimized using the software to provide recommendations on how the initial arrangement of separators/bins may be altered for improved functionality.

In accordance with yet another aspect of the present invention, the system may further learn from each created layout of bins/separators using machine learning/artificial intelligence and associate each layout against specific items, specific users, or specific models of automated dispensing systems. Such correlations may further be utilized to enable the system to learn and provide a more effective layout of the separators/bins where each new recommended configuration of the layout is a better-informed layout that consider all the past created layouts and configuration of separators/bins in trays. It may further be envisioned to create, maintain and share a library of such preferred layouts and configurations across multiple installations and offer customers the ability to subscribe to gain access to such library of tray layouts and configurations mapped by the type, size, shape, volume and format of the items as well as by the class of the automated dispensing system, user, or procedure.

Figure 10:
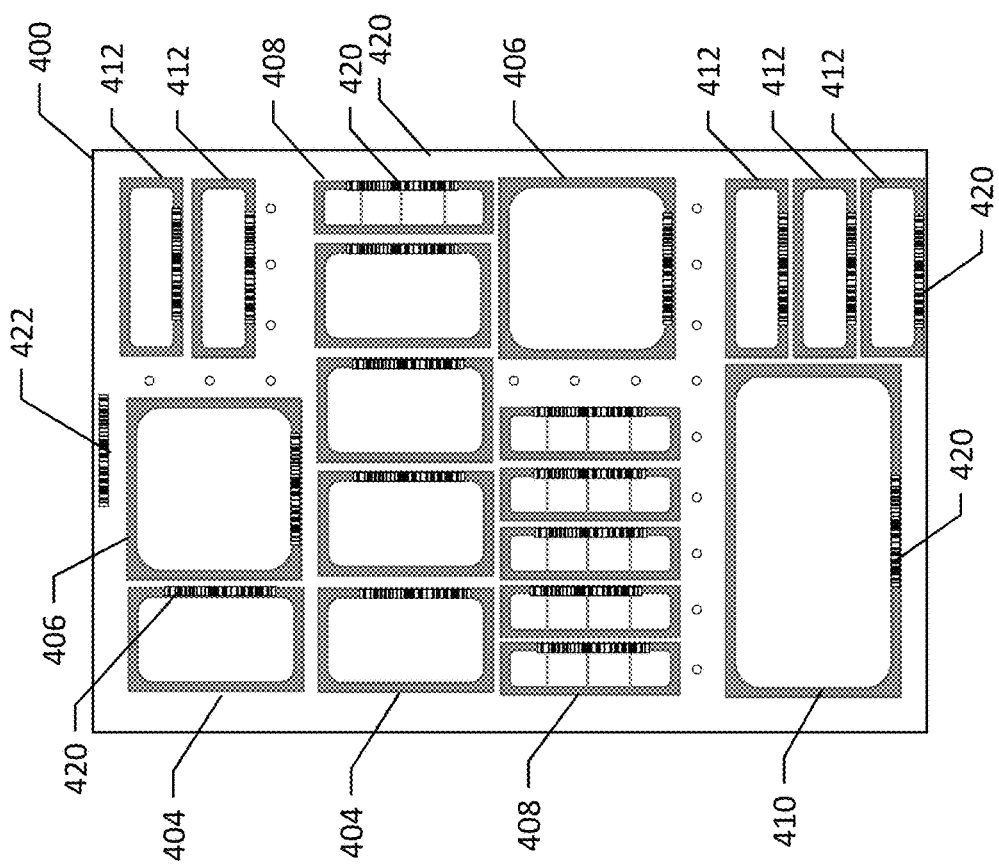
FIG. 10 depicts a plurality of uniquely identifiable bins arranged on a tray according to an example embodiment of the present disclosure.

According to some embodiments, each bin may have a unique identifier. The unique identifier may include a radio frequency identification (RFID) tag or a barcode, for example. FIG. 10 illustrates such an embodiment in which a tray 400 includes a plurality of bins (404-412) where each bin has a unique barcode identifier 420. This unique bin identifier may be used to associate each bin with an article received within the bin. The bins may be loaded through automated or manual means, and each bin may be correlated with the article received within the bin as it is loaded. For example, in an automated loading process, a robot may load a bin with a product specified for the tray and scan the identifier 420 of the bin as it is loaded. Alternatively, in a manual operation a user may scan the identification of an article that is being loaded and scan the identifier 420 of the bin into which the product is loaded. In this manner, each product in the tray is uniquely associated with a uniquely identified bin. Such an association allows for more accurate tracking of bin contents and tray contents, while also facilitating accurate dispensing of articles from bins. When an article is dispensed, the bin identifier 420 may be scanned for confirmation of retrieval of the appropriate article.

Embodiments described herein may optionally include a unique identifier 422 on the tray 400 itself. Such an identifier may uniquely identify the tray which may then inform a user of the contents of the tray. Further, trays may be customized and built according to a specific configuration that may be needed for a particular use. The trays may be stored in a storage location and retrieved as the need for trays of a specific configuration arises. For example, a tray may include a configuration for articles specifically identified for treatment of flu sufferers. Such a tray may not be needed at all times during a year, and a nurse cart may require multiples of such trays during peak flu season. In such an embodiment, a uniquely identified tray configured to store articles specifically identified for flu sufferers may be stored offboard the nurse carts when the flu is not prevalent in an area, and retrieved for use in nurse carts during the flu season.

The user interfaces of controllers used to build tray configurations may be in communication, such as via communication interface 236, with a service provider which may provide software updates and fixes as needed. Further, the service provider may use data from the controllers to better serve customers. For example, the service provider may identify commonalities among customized trays built by different customers, and use these identified commonalities to build trays uniquely adapted for use with different types of customers. A nursing home facility may build custom trays for their patients of a first configuration, where that configuration shares many common features with custom trays built at other nursing home facilities. The service provider may identify these commonalities and build trays uniquely configured for nursing home facilities. This may include unique bins adapted for the nursing home facility needs, for example.

According to an example embodiment, each location of a tray may be uniquely identified, such as through the barcodes 420 of FIG. 10, such that a position of the location within the tray is known. The geometry of a tray generated by the software of example embodiments and the locations therein may be stored within a memory, such as memory 232 of the controller illustrated in FIG. 2. Each tray may be unique such that the memory 232 includes a unique layout and geometry together with location identifiers for each tray. In such an embodiment, each tray may include a unique identifier, such as a barcode, 2-dimensional barcode, an RFID tag, etc. Optionally, there may be a specific number of configurations of trays, and each configuration may have a unique identification. In such an embodiment, the identification of a tray may only provide the configuration information, while the location of the tray within the storage module may be stored within the memory of the controller 232 to facilitate retrieval of articles from the tray.

In an example embodiment of an automated storage system, such as the automated dispensing system 200 of FIG. 3, the trays 400 may be maintained within or associated with a particular storage module, such that the trays are replenished for dispensing of articles therefrom. However, according to some embodiments, the trays may be removable from the storage modules and replenishment may occur through replacement of trays within a storage module. In such a case where trays are removable from a storage module, an identification of a tray 422 may be read by a device, such as a scanning device, upon receipt into a storage module such that the controller can associate a specific tray with a specific location within the automated storage device.

As articles are dispensed from automated dispensing systems as described herein, replenishment of articles is required to maintain an inventory of articles for dispensing. The replenishment is an operation that may occur in downtime between dispensing operations, which may occur overnight in a healthcare facility where fewer medications are being dispensed, for example. Various methods for replenishment may be used to replenish the automated dispensing systems described herein, and replenishment in a fast and efficient manner may be important in implementations in which there is little downtime over which replenishment may occur.

The automated dispensing system 200 of example embodiments may also provide automated replenishment using the robot 204 and end-of-arm tool 208 as described herein. Replenishment may occur through replacement of entire trays 400, or portions thereof. For example, a replenishment cart may be received within cart module 218, where the replenishment cart includes a plurality of trays stored therein, which may be customized as described above. These trays may include a plurality of customized storage locations as described above with respect to FIG. 10. The trays may be removable from the cart, such that a tray may be retrieved by the robot 204. The trays 400 of the replenishment cart may be of the same size as the trays 212 of the storage module 202, and may be interchangeable with the trays of the storage module. In such an embodiment, replenishment may occur through the swapping of trays within the storage module with a replacement tray from the replenishment cart.

The robot 204 may include a scanner, such as a barcode scanner, RFID tag scanner/reader, etc., to read the identification of articles as they are retrieved and/or placed into storage locations. Further, this scanner may read the identification 422 of trays 400 and/or the identification 420 of bins within the trays. The scanner may be used to identify articles that are being dispensed or replenished in order to ensure accuracy and that the article that is stored in a particular location of the storage module is consistent with the article that is anticipated.

In accordance with another embodiment of the present system, the configuration tool can take as input an already created user layout, use algorithms to analyze if the configuration of the tray is optimal or if a recommendation can be made to alter the configuration. In accordance with yet another embodiment of the present system, a user may create a configuration map based on their personal preference and upload that configuration for the dispensing system to consider. Such an embodiment would afford the user an opportunity to create a preferred tray layout, while the dispensing system may offer recommendations for optimizing the tray layout. Users, such as pharmacy technicians, may optionally arrange a plurality of articles on a tray, whereby a layout can be generated based on the arranged articles. In such an embodiment, separators could be assembled around the articles to form the layout and bins Such an embodiment may use an image capture device to capture an image of the arranged articles and to identify locations for bin edges or separators.

According to an example embodiment, an automated dispensing system 200 may be in communication with the configurator module 130 such that the automated dispensing system may provide input for the configurator module. The automated dispensing system may identify available space within the system such that the configurator module 130 may identify articles needed by the system and prioritize those articles based on the amount of space available within the system. The automated dispensing system 200 may provide input to the configurator 130 to enable maximum flexibility of the layout of different trays according to needs of the system. Further, existing trays within the automated dispensing system may be re-configured as needed to make use of available space and/or to logically arrange articles according to their historical use.

Figure 11:
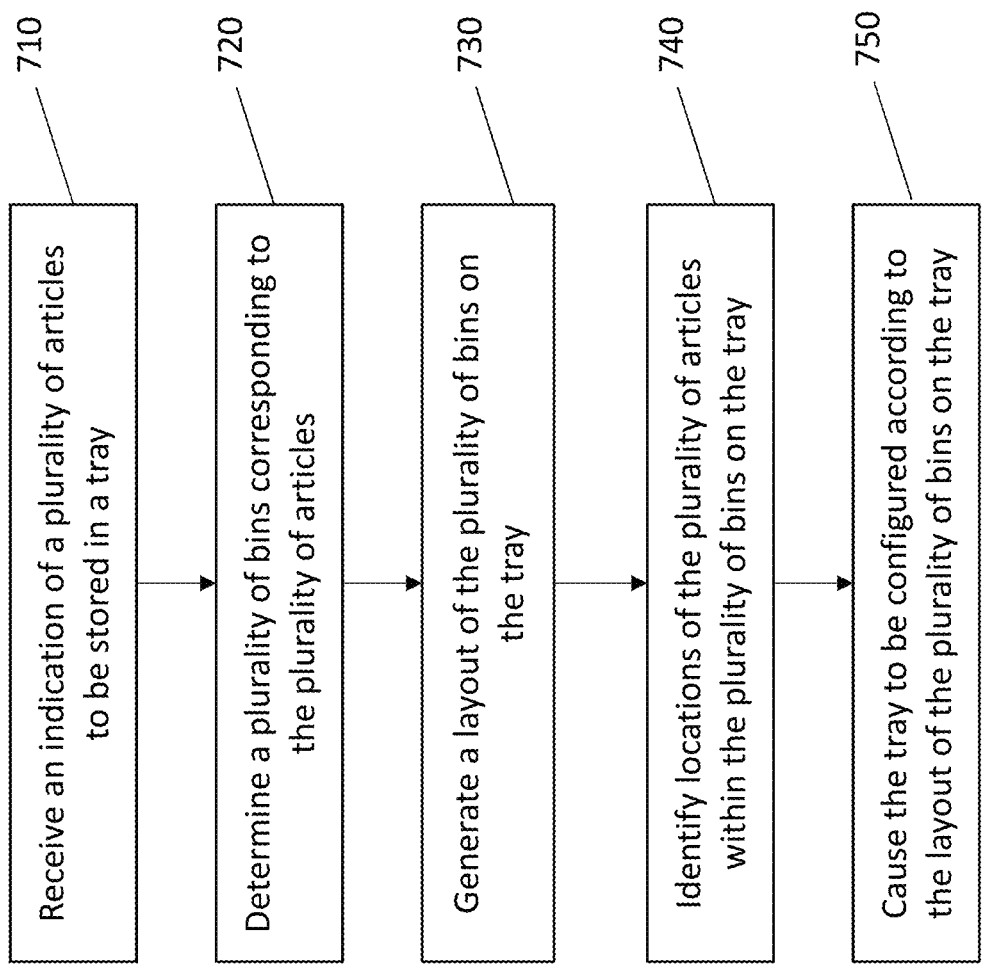
FIG. 11 illustrates is a flowchart of a method of operating an automated dispensing system according to an example embodiment of the present disclosure.

FIG. 11 is a flowchart of a method and program product according to an example embodiment of the present disclosure. It will be understood that each block of the flowchart and combinations of blocks in the flowchart may be implemented by various means, such as hardware, firmware, processor, circuitry, and/or other devices associated with execution of software including one or more computer program instructions. These computer program instructions may also be stored in a non-transitory computer-readable memory that may direct a computer or other programmable apparatus to function in a particular manner, such that the instructions stored in the computer-readable memory produce an article of manufacture which implements the functions specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In this regard, a method according to one embodiment of the disclosure, as shown in FIG. 11, may include receiving an indication of a plurality of articles to be stored in a tray at 710. A plurality of bins corresponding to the plurality of articles may be determined at 720. In some instances, a plurality of separators may be determined to form the plurality the bins. A layout of the plurality of bins on the tray may be generated at 730. Locations for the articles within the plurality of bins on the tray may be identified as shown at 740. The tray may be configured according to the layout of the plurality of bins on the tray as shown at 750.

In another exemplary method of use of the invention as disclosed hereinabove, the method may involve the steps of a user providing as input, an initial configuration of layout on a tray using one or more separators to form one or more storage areas that resemble one or more bins. This input may be processed using specific algorithms to optimize the initial configuration of layout on the tray and create a final, improved, better optimized layout on the tray either by re-orienting, or re-sizing, or providing additional recommendations for new separators to form new storage areas. Alternately, the algorithm may also recommended an optimization that involves reducing the number of storage areas.

While example embodiments described above include bin layout and separator layout to optimize the layout to accommodate a predefined inventory, embodiments described herein may include bin/separator layout that is optimized based on different priorities. For example, one strategy for bin/separator layout optimization includes optimizing the layout for speed of access and retrieval of articles within the tray. In such an embodiment, the layout geometry may be designed to make use of robot arm positions of a retrieving robot that enhance speed and arm orientation that reduces cycle time. A retrieval robot may have axis acceleration and velocity profiles that can be used to identify motions that are most efficient for the robot, and those motions may correspond to certain tray positions. Accordingly, a tray layout may be designed to capitalize on these tray positions and improve the speed and efficiency of article retrieval.

Other bin/separator layout optimization strategies may include improving article density. While a first layout may store a first number of articles, embodiments of a density optimization strategy may reconfigure the layout to be able to store a second number of articles, larger than the first number of articles.

The bin/separator layout optimization strategy may optionally be used to improve energy efficiency of robot retrieval. For example, the article containment geometry may be modified to move fast-moving, high-demand articles to a more accessible position on a tray, such as proximate a front of the tray closest to the retrieval robot such that energy consumption and distance traveled by the robot arm may be reduced relative to accessing articles at a back of a tray, further from the robot.

The layout of bins and separators may optionally be influenced by other bin/separator layouts used by other trays, which may include trays from other facilities. Tray layouts may be established by other facilities that improve throughput by pairing certain types of medications within a tray when they are commonly used together, for example. Thus, access to the associated medications is more efficient and the speed of retrieval improved. Further, efficient layout configurations for various types of article trays (e.g., seasonally demanded medications, medications associated with certain procedures, etc.) may be generated at a first facility and recognized by the system as improving throughput efficiency based on a history of retrieval from the tray layout. This tray layout may then be shared with other facilities that may benefit from a similar layout. This provides an example of crowd-sourcing or cloud-sharing of tray layout configurations that promotes improvements in efficiency across a population of facilities.

In addition to bin/separator layout efficiency improvements, embodiments may be configured to identify tray location movement to improve efficiency. A tray may be moved within an automated dispensing system based on a frequency of access, such that more frequently accessed trays may be moved to positions that are more easily and efficiently accessed than those that may be used to store lower-demand articles. Such an optimization may result in less movement of a retrieval robot thereby improving throughput while also reducing power consumption.

In some embodiments, certain ones of the operations may be modified or further amplified as described below. Moreover, in some embodiments additional operations may also be included. It should be appreciated that each of the modifications, optional additions, or amplifications below may be included with the operations above either alone or in combination with any others among the features described herein.

In an example embodiment, an apparatus for performing the method of FIG. 11 may include a processor configured to perform some or all of the operations (710-750) described above. The processor may, for example, be configured to perform the operations (710-750) by performing hardware implemented logical functions executing stored instructions, or executing algorithms for performing each of the operations. Alternatively, the apparatus may include means for performing each of the operations described above.

An example of an apparatus according to an example embodiment may include at least one processor and at least one memory including computer program code. The at least one memory and the computer program code may be configured to, with the at least one processor, cause the apparatus to perform the operations 710-750.

An example of a computer program product according to an example embodiment may include at least one computer-readable storage medium having computer-executable program code portions stored therein. The computer-executable program code portions may include program code instructions for performing operations 710-750.

Many modifications and other embodiments of the inventions set forth herein will come to mind to one skilled in the art to which these inventions pertain having the benefit of the That which is claimed:

1. A system, comprising:
a configuration interface adapted to receive at least one input parameter to determine a storage configuration for one or more trays adapted to engage with a dispensing system, each of the one or more trays adapted to store one or more articles;
a configurator module, further comprising processing circuitry, adapted to generate a recommended storage configuration layout for the one or more trays for securely holding the one or more articles based on the at least one input parameter; and
a controller configured to:
determine if the one or more trays are configured according to the recommended storage configuration layout; and
provide an alert in response to the one or more trays not being configured according to the recommended storage configuration layout,
wherein for each of the one or more articles, the at least one input parameter includes at least one of the following: type of the article, size of the article, capacity of the article, identification of the article, volume of contents held within the article, and available space in the dispensing system.

2. The system of claim 1, wherein the recommended layout for the one or more trays specifies at least one of: number of separators, orientation of the separators, or location of placement of the separators.

3. The system of claim 1, wherein the recommended layout for each of the one or more trays comprises a recommended layout of bins and specifies at least one of: a number of bins, a size for each of the bins, a quantity of the one or more articles that can be held within each of the bins, a number of trays needed to hold the one or more articles, and a relative positioning of the one or more bins within the recommended layout.

4. The system of claim 3, wherein the processing circuitry is further configured to:
receive an indication of an article to be loaded into a bin of the layout of bins;
receive a unique identifier of the bin of the layout of bins into which the article is loaded; and
store, in a memory, a correlation between the unique identifier of the bin and the article loaded into the bin.

5. The system of claim 4, wherein the processing circuitry is further configured to:
receive an indication of a unique identifier of a tray corresponding to the layout of bins; and
correlate the unique identifier of the bin and the article loaded into the bin with the unique identifier of the tray.

6. The system of claim 3, wherein the processing circuitry configured to generate the recommended layout of bins for securely holding the one or more articles comprises processing circuitry configured to:
determine a size of each of the one or more articles; and
identify, for each of the one or more articles, a bin size appropriate for the respective article.

7. The system of claim 1, wherein the processing circuitry configured to generate a recommended layout comprises processing circuitry configured to:
generate a recommended layout using one or more separators forming one or more bins on a tray, the layout further comprising a position and an orientation for the one or more bins on the tray.

8. The system of claim 1, wherein the configuration interface to receive at least one input parameter to determine a storage configuration for the one or more trays comprises:
a user interface element to select a type of article;
a user interface element to select a quantity of a type of article; and
a user interface element to add the quantity of the type of article to a list of the one or more articles to be stored in a tray.

9. The system of claim 1, wherein the processing circuitry is further configured to:
provide instruction for configuration of the recommended layout for the one or more trays; and
cause the configuration of the recommended layout for the one or more trays to be assembled.

10. The system of claim 1, wherein the processing circuitry is further configured to:
cause the one or more articles to be dispensed and arranged according to the recommended layout.

11. The system of claim 1, further comprising an image capture device configured to capture an image of the one or more trays, wherein the controller configured to determine if the one or more trays are configured according to the recommended storage configuration layout is configured to determine, from the image of the one or more trays, if the one or more trays are configured according to the recommended storage configuration layout.

12. A method for configuring one or more trays, comprising:
receiving information about one or more articles to be stored in the one or more trays;
selecting one or more separators or bins to hold the one or more articles based on data representing characteristics of at least the one or more items and characteristics of the one or more trays;
determining a layout map for the one or more trays using at least characteristics of the one or more articles;
generating a tray layout for a tray to hold the one or more articles based on the layout map;
determining if the tray layout for a configured tray is configured according to the layout map; and
providing an alert in response to the configured tray not being configured according to the layout map.

13. The method of claim 12, further comprising:
identifying locations for the one or more articles within the tray layout; and
causing the one or more trays to be configured according to the tray layout.

14. The method of claim 13, further comprising:
receiving an indication of an article to be loaded into a location within the tray layout;

receiving a unique identifier of the location into which the article is loaded; and storing, in a memory, a correlation between the unique identifier of the location and the article loaded into the location.

15. The method of claim 14, further comprising:

receiving an indication of a unique identifier of a tray corresponding to the location into which the article is loaded; and correlating the unique identifier of the location and the article loaded into the location with the unique identifier of the tray.

16. The method of claim 12, wherein determining the layout map for the tray comprises:

determining a size of each of the one or more articles; and identifying, for each of the one or more articles, a bin size appropriate for the respective article.

17. The method of claim 12, wherein generating the layout map for the one or more trays comprises:

generating a layout of the one or more separators or bins on the tray including a position and an orientation of the one or more separators or bins on the tray.

18. The method of claim 12, wherein receiving information about one or more articles to be stored in the one or more trays comprises:

receiving selection of a type of article;

receiving selection of a quantity of the type of article; and receiving an indication to add the quantity of the type of article to a list of the plurality of articles to be stored in the one or more trays.

19. The method of claim 12, further comprising:

providing instruction for configuration of the layout map for the one or more trays; and causing the configuration of the layout map to be assembled.

20. An apparatus comprising at least one processor and at least one non-transitory computer readable storage medium comprising program code instructions stored thereon, the at least one processor configured to, upon execution of the program code instructions, cause the apparatus to at least:

receive an indication of a plurality of articles to be stored in a tray;

determine a plurality of bins corresponding to the plurality of articles;

generate a layout of the plurality of bins on the tray;

identify locations of the plurality of articles within the plurality of bins on the tray;

cause the tray to be configured according to the layout of the plurality of bins on the tray;

determine if a configured tray is configured according to the layout map; and provide an alert in response to the configured tray not being configured according to the layout map.

* * * * *